United States Patent [19]

Najer et al.

[11] Patent Number: 4,663,340
[45] Date of Patent: May 5, 1987

[54] ALPHA-ADRENORECEPTOR AGONISTIC 2-[(2-CYCLOPROPYL-5-METHYL- OR 2-CYCLOPROPYL-5-CHLOROPHENOXY)-METHYL]-2-IMIDAZOLINES

[76] Inventors: Henry Najer, 2, Avenue Emile Acollas, 75007 Paris; Jean-François Giudicelli, 17, rue du clos d'Orl',acu/e/ ans, 94120 Fontenay-sous-Bois; Jean-Claude Dufour, 4 Rond-Point Saint-James, 92200 Neuilly-sur-Seine, all of France

[21] Appl. No.: 752,250

[22] Filed: Jul. 3, 1985

[30] Foreign Application Priority Data

Jul. 13, 1984 [FR] France .................................. 84 11271

[51] Int. Cl.[4] .................... A61K 31/415; C07D 233/22
[52] U.S. Cl. ....................................... 514/401; 548/353
[58] Field of Search ........................... 548/353; 514/401

[56] References Cited

U.S. PATENT DOCUMENTS 2,149,473 3/1939 Sonn ..................................... 548/353
2,915,431 12/1959 Carron et al. ....................... 548/353
3,449,355 6/1969 White ................................... 548/353

FOREIGN PATENT DOCUMENTS

A2394531 1/1979 France ................................ 548/353

OTHER PUBLICATIONS

Dharmsathaphorn et al., Gastroenterology, 86, pp. 120–128 (1984).
Chemical Abstracts, vol. 100, No. 13, 96148m, 1984.

Primary Examiner—John M. Ford
Assistant Examiner—Kurt G. Briscoe
Attorney, Agent, or Firm—Ladas & Parry

[57] ABSTRACT

The present invention relates to imidazolines of general formula (I)

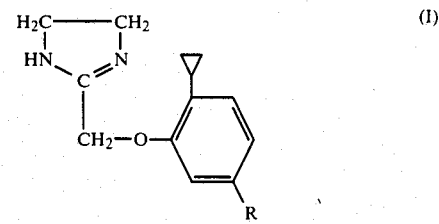

and the addition salts formed therefrom with the pharmaceutically acceptable mineral or organic acids, possibly having their own specific pharmacological properties.

The invention further relates to the preparation of these products, to their use as new medicines and to the medicinal compositions containing them.

4 Claims, No Drawings

ALPHA-ADRENORECEPTOR AGONISTIC 2-[(2-CYCLOPROPYL-5-METHYL- OR 2-CYCLOPROPYL-5-CHLOROPHENOXY)METHYL]-2-IMIDAZOLINES

The present invention relates to novel imidazolines of general formula (I)

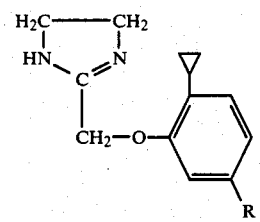
(I)

and the addition salts formed therefrom with the pharmaceutically acceptable mineral or organic acids, some of which, such as the hydrochloric, sulphuric, nitric, acetic, tartric, citric and other acids, have no special pharmacological properties, whereas others have a therapeutic activity which is complementary to that of compounds (I), such as the prednisolone-21-benzoyl-metasulphonic acid; 9α-fluoro-16β-methyl-11β,17α,21-trihydroxy-1,4-pregnadiene-3,20-dione-21-orthophosphoric acid; 11β,17α,21-trihydroxy-1,4-pregnadiene-3,20-dione-21-orthophosphoric acid; 11β,17α,21-trihydroxy-4-pregnene-3,20-dione-21-orthophosphoric acid; 11β,17α,21-trihydroxy-4-pregnene-3,20-dione-21-succinic acid; this list being in no way restrictive.

The present invention further relates to the process for the preparation of imidazolines (I), as well as to their use as new medicines and to the medicinal composition containing them.

The invention therefore relates to the compounds of general formula (I) in which R is:
an alkyl group with 1 to 5 straight or branched carbon atoms, or
an halogen atom, such as chlorine or bromine.

Said compounds, and in particular that wherein R is a methyl residue, namely the (5'-methyl-2'-cyclopropyl)-2-phenyloxymethyl-Δ$_2$-imidazoline and that wherein R is a chlorine atom, namely the (5'-chloro-2'-cyclopropyl)-2-phenyloxymethyl-Δ$_2$-imidazoline, have proved to have quite remarkable and unexpected properties.

French Pat. No. 2 145 423 describes (2'-cyclopropyl)-2-phenyloxymethyl-Δ$_2$-imidazoline, now known under the common designation "Cirazoline", as a powerful nasal vasoconstrictor. This vasoconstrictor activity is due to a postsynatpic α$_1$-adrenoceptor agonist activity.

Quite unexpectedly, the imidazolines (I), and in particular those in which R=CH$_3$ or Cl, have been found to exhibit more powerful and more specific postsynaptic α$_1$-adrenoceptor agonist properties than Cirazoline.

At the presynaptic level, on the contrary, neither the imidazolines (I) nor in fact Cirazoline, exhibit any α$_2$-adrenoceptor agonist or antagonist actions.

The present invention therefore relates also to the drugs containing as active product, at least one compound of formula (I). Said drugs are especially useful as vasoconstrictors and nasal congestion-relieving agents. When the salts are produced from acids having a specific therapeutic property, the resulting product has the properties of the two constituents of said salts and often they have improved properties towards rhinological syndromes.

The invention further relates to the process for preparing the derivatives (I) according to process diagram (A) or variants thereof, such as for example (B).

Diagram (A)

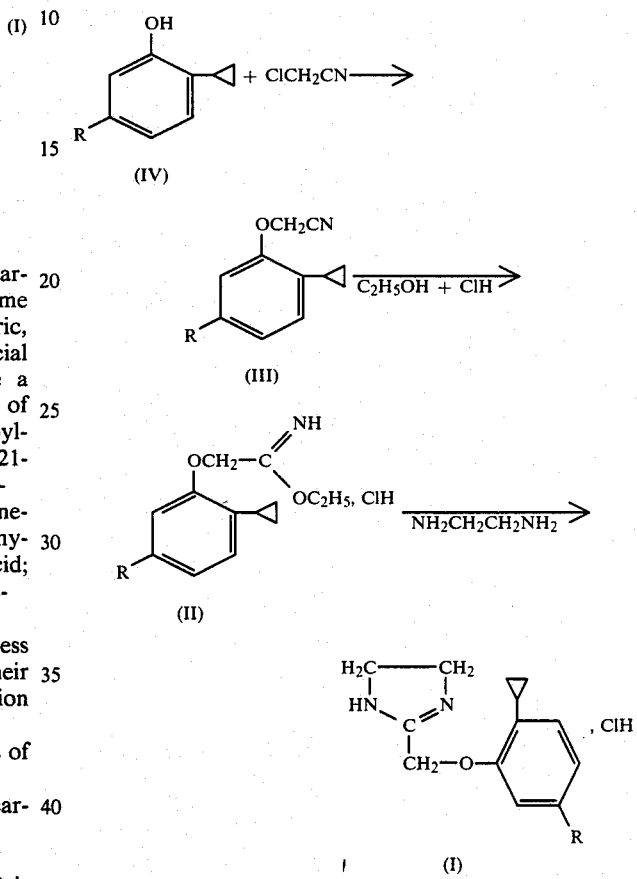

Variant (B)

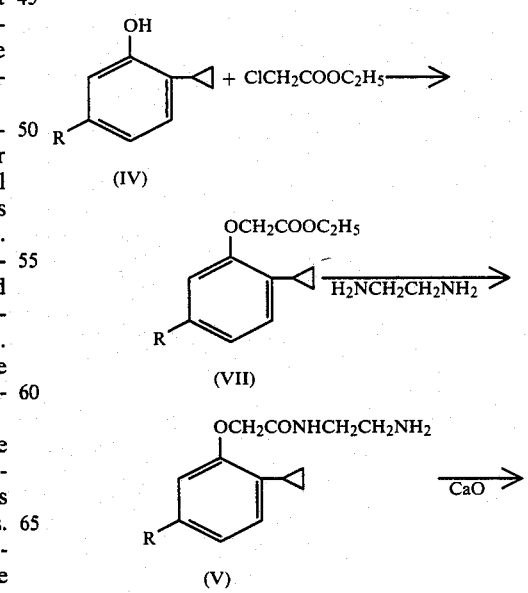

-continued

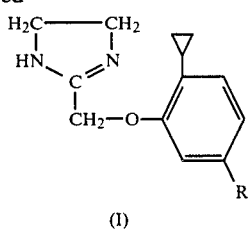

R being as defined hereinabove.

The process according to diagram (A) consists in reacting diamine ethylene with an iminoether of general formula (II). The reaction generally takes place in an alcohol of low molecular weight, preferably ethyl alcohol, and at solvent reflux temperature, the heating period lasting a few hours, and preferably four to six hours.

The iminoether (II) is prepared by condensing a nitrile of general formule (III) with an equimolecular quantity of an alcohol, preferaly ethyl alcohol, in an inert solvent such as ether, a stream of hydrochloric acid being passed through that solution until saturation. Condensation takes place at low temperature, between 0° and 10° C., the mixture being left to stand for twelve to twenty-four hours. The imino-ether hydrochlorate (II) is recovered either by draining the precipitate, or by evaporating the solvent in vacuo at low temperature.

The nitriles (III) are prepared by heating one molecule of a phenol of general formula (IV) and 1.5 molecules of chloracetonitrile inside an inert solvent, preferably methyl ethyl ketone and in the presence of an hydrochloric acid acceptor, preferably an alkaline carbonate such as potassium carbonate. The heating temperature is the solvent reflux temperature and the heating period is several hours, preferably around 10 hours.

The process according to variant (B) consists in heating an amido-amine of general formula (V) to a temperature of 150°–200° C. in the presence of quick lime.

The amido-amines (V) are prepared by condensing an ester of general formula (VI) with a large excess of ethylene diamine at 100°, the heating period being several hours, preferably between ten and twenty-four hours.

The esters (VII) are prepared by heating a molecule of a phenol (IV) and 1.5 molecules of ethyl chloroacetate in an inert solvent, preferably methyl ethyl ketone, and in the presence of an hydrochloric acid acceptor, preferably an alkaline carbonate such as potassium carbonate. The heating temperature is the reflux temperature of the solvent used and the heating period is several hours, preferably about twenty hours.

The invention further relates to phenols of general formula (IV) as intermediate products in the preparation of imidazolines (I). They are obtained from substituted anilines of general formula (VIII)

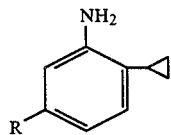

in which R is as indicated hereinabove, by treatment with sodium nitrite in an acid medium, followed by heating and steam distillation.

The salts from the imidazolines (I) object of the present invention are obtained by any of the known processes used for preparing addition salts.

A number of examples of embodiments are given hereinafter to illustrate the preparation of the products according to the invention, on the understanding that the precisions given concerning the operational conditions such as temperature, reaction time, nature of the solvent, as well as concerning the relative proportions of the reagents used, are not in any way restrictive.

EXAMPLE 1

HYDROCHLORIDE OF (5'-METHYL-2'-CYCLOPROPYL)-2 PHENYLOXYMETHYL-$\Delta_2$IMIDAZOLINE (I) (R=CH$_3$) (N.D. 83.201)

(a) 5-methyl-2-cyclopropyl phenol:

73.5 cm3 of water and 10.5 cm3 of concentrated sulphuric acid are introduced in a 500 cm3 three-nozzled flask, equipped with a bromine funnel, a thermometer, mechanical stirring means and a reflux condenser. Then 17.2 g (0.117 mole) of 5-methyl-2-cyclopropyl aniline are added dropwise, in about 15 minutes, through the bromine funnel. The mixture is then brought to a temperature of 60° C. to dissolve the salt which has formed. The solution is thereafter cooled down to 0° C. under strong stirring and a solution of 7.8 g (0.117 mol/g) of sodium nitrite in 10.5 cm3 of iced water is added through the bromine funnel in one hour. The temperature of the reaction mixture is allowed to return to ambient temperature, and is then brought to between 50° C. and 60° C. for 30 minutes (end of release of nitrous vapors). Said mixture is then allowed to cool and the phenol which has formed is steam distillated.

The distillate is extracted twice successively with 200 cm3 of methylene chloride, the collected extracts are dried over dry sodium sulphate, filtered, then the solvent is evaporated and the residue is fractionated.

8.1 (yield: 58%) of 5-methyl-2-cyclopropyl phenol are finally obtained, boiling between 64°–70° C. under 0.1 mm mercury.

(b) 5-methyl-2-cyclopropyl-phenoxyacetonitrile:

In a 250 cm3 three-nozzled flask equipped with mechnical stirring means, a sinking thermometer, a bromine funnel and a condenser topped by a drying tube filled with calcium chloride, 13.2 g (0.0891 mol/g) of 5-methyl-2-cyclopropyl-phenol are introduced together with 90 cm3 of methyl ethyl ketone dried on siliporite and 13.8 g (0.1 mol/g) of potassium carbonate. 9.1 cm3 of chloroacetonitrile are added through the bromine funnel, and the resulting mixture is brought for 7 hours to the reflux temperature. It is left to stand overnight at room temperature, then an insoluble substance is filtered, and washed with 100 cm3 of methyl ethyl ketone which is then evaporated from the filtrate. 100 cm3 of anhydrous ether dried over siliporite are added to the residue, and the solution is stirred strongly, then an insoluble substance is filtered off and washed with 70 cm3 of anhydrous ether, then the ethereal phases are collected, washed twice successively with 70 cm3 of sodium hydroxyde N, the aqueous phases are extracted four successive times with 50 cm3 of ether, and the collected ethereal phases are washed with four times 50 cm3 of water, and dried over sodium sulphate, then filtered, and the solvent is evaporated and the residue fractionated. 11 g (yield: 66.5%) of 5-methyl-2-cyclopropyl phenoxyacetonitrile are finally obtained boiling between 113° C.–117° C. under 0.5 mm mercury.

(c) Hydrochloride of ethylic imino-ether of (5-methyl-2-cyclopropyl)phenoxy acetic acid:

8.2 g (0.045 mol/g) of 5-methyl-2-cyclopropyl-phenoxyacetonitrile, 2.8 cm3 of anhydrous ethanol and 50 cm3 of ether dried over siliporite are introduced under nitrogen atmosphere, in a 250 cm3 three-nozzled flask, equipped with a condenser topped with a drying tube filled with calcium chloride. The mixture is cooled to 0° C. and a stream of hydrochloric acid is caused to bubble through until saturation (about 7 hours). The reaction mixture is then left to stand overnight at room temperature, and the precipitated imino-ether hydrochlorate is drained, washed with 50 cm3 of anhydrous ether and dried in the open.

10.3 g (yield: 86%) of hydrochloride of ethylic imino-ether of (5-methyl-2-cyclopropyl-2-phenoxy)acetic acid are finally obtained in the form of a non-hygroscopic white solid.

(d) Hydrochloride of (5'-methyl-2'-cyclopropyl)-2-phenyloxymethyl-$\Delta_2$-imidazoline:

10.3 g (0.038 mol/g) of hydrochloride of ethylic imino-ether of (5-methyl-2-cyclopropyl-phenoxy)acetic acid and 40 cm3 of anhydrous ethanol are introduced under nitrogen atmosphere in a 250 cm3 five-nozzled flask, equipped with a condenser topped with a drying tube filled with calcium chloride, with stirring means, a bromine funnel, and a sinking thermometre. 2.2 cm3 of diamine ethylene, distilled beforehand on potassium hydroxide and dried over siliporite are poured through the bromine funnel, the mixture strongly stirred. Said mixture is then brought for 6 hours at reflux temperature. An insoluble substance is filtered off and wash with 100 cm3 of anhydrous alcohol, and the solvent is evaporated from the filtrate, the residue is triturated with 50 cm3 of acetone, previously distilled on potassium hydroxide and dried over siliporite, after what the precipitate is drained and then washed with 75 cm3 of anhydrous acetone.

4.6 g (yield: 45%) of (5'-methyl-2'-cyclopropyl)-2-phenoxymethyl-$\Delta_2$-imidazoline hydrochloride are finally obtained, which, after being re-crystallized in 30 times their weight of isopropanol, are in the form of a white substance, which is not very soluble in water and which melts at between 212° C. and 218° C.

EXAMPLE 2

HYDROCHLORIDE OF (5'-n-pentyl-2'-cyclopropyl)-2-phenyloxymethyl-$\Delta_2$-imidazoline (I) 5=C$_5$H$_{11}$n) (N.D. 83.203)

(a) n-5-pentyl-2-cyclopropyl-phenol

Prepared in the same conditions as its 5-methyl homolog of Example 1 from 10.5 g (0.053 mol/g) of n-5-pentyl-2-cyclopropylaniline with a gross yield of 42.5% which is used as is in the next reaction.

(b) 5-n-pentyl-cyclopropyl-phenoxyacetonitrile

Prepared in the same conditions as its homolog 5-methyl of Example I from 5.1 g (0.025 mol/g) gross of 5-n-pentyl-2-cyclopropyl phenol with a gross yield of 85.5% which is used as is in the next reaction:

(c) Hydrochloride of ethylic imino-ether of 5-n-pentyl-2-cyclopropyl phenoxyacetic acid:

Prepared in the same conditions as its 5-methyl homolog of Example I from 5.2 g (0.0214 mol/g) of 5-n-pentyl-2-cyclopropylphenoxy-acetonitrile. When re-crystallized in isopropanol, the imino-ether hydrochlorate is in the form of a non-hygroscopic white powder which melts at 100° C. Yield: 40%.

(d) Hydrochloride of (5'-n-pentyl-2'-cyclopropyl)-2-phenyloxymethyl-$\Delta_2$-imidazoline Prepared in the same conditions as its 5-methyl homolog of Example I from 2.8 g (0.0086 mol/g) of ethylic imino-ether hydrochloride of 5-n-pentyl-2-cyclopropyl-phenoxyacetic acid with a yield of 54%. M.P. 214° C. (isopropanol).

EXAMPLE 3

HYDROCHLORIDE OF (5'-CHLORO-2'-CYCLOPROPYL)-2-PHENOXYMETHYL-$\Delta_2$-IMIDAZOLINE (R=Cl) (N.D. 83.204)

(a) 5-chloro-2-cyclopropyl phenol

Prepared according to the method described for the 5-methyl-2-cyclopropyl-phenol of Example I, from 31.5 g (0.188 mol/g) of 5-chloro-2-cyclopropyl-aniline with a yield of 32%. B.P.=69° C.–76° C./0.1 mm mercury. m.P. 30° C.

(b) 5-chloro-2-cyclopropyl-phenoxyacetonitrile

Prepared according to the method described in Example I (b) from 6 g (0.0356 mol/g) of 5-chloro-2-cyclopropyl-phenol with a gross yield of 95%. The crude product is used in the next reaction:

(c) Hydrochloride of ethylic imino-ether of 5-chloro-2-cyclopropylphenoxy acetic acid:

9 g (yield: 92%) of hydrochlorate of imino ether are obtained from 7 g of the above crude nitrile according to the method described in Example (1 c).

(d) Hydrochloride of (5'-chloro-2'-cyclopropyl)-2-phenoxy-methyl-$\Delta_2$-imidazoline 9 g (0.031 mol/g) of the imino-ether hydrochloride obtained above are reacted according to the method described in Example 1 (d), with 1.7 g (0.0282 mol/g) of anhydrous diamine ethylene in 35 cm3 of absolute alcohol. The reaction medium is heated to the reflux temperature for 6 hours, then the alcohol is evaporated. The residue is triturated in 30 cm3 of water, drained, then the precipitate is washed successively in first 40 cm3 and then in three times 20 cm3 of acetone, after what it is dried in the open and finally recrystallized in methanol.

3.2 g (yield: 36%) of hydrochloride of (5'-chloro-2'-cyclopropyl)-2-phenoxymethyl-$\Delta_2$-imidazoline are obtained in the form of a white compound, not very soluble in water, M.P. 248° C.–250° C.

EXAMPLE 4

HYDROCHLORIDE OF (5'BROMO-2'-CYCLOPROPYL)-2-PHENOXYMETHYL-$\Delta_2$-IMIDAZOLINE (I) (R=Br) (N.D. b 83.203)

(a) 2-bromo-2-cyclopropyl-phenol

Prepared by the method described in Example 1(a) from 17 g (0.08 mol/g) of 5-bromo-2-cyclopropyl-aniline with a yield of 25%. White crystals are obtained which melt at 46° C.

(b) 5-bromo-2-cyclopropyl-phenoxyacetonitrile

Prepared according to the method described in Example 1(b) from 6.6 g (0.04 mol/g) of 5-bromo-2-cyclopropyl-phenol with a yield, after rectification, of 76%. A colorless liquid is obtained boiling between 120° C. and 128° C. under a vacuum of 0.5 mm of mercury.

(c) Hydrochloride of ethylic imino-ether of 5-bromo-2-cyclopropylphenoxyacetic acid Prepared from the nitrile described above according to the method of Example 1(c) with a yield of 92%.

(d) Hydrochloride of (5'-bromo-2'-cyclopropyl)-2-phenoxymethyl-$\Delta_2$-imidazoline Prepared from 7.1 g (0.021 mol/g) of the above imino-ether hydrochloride and 1.16 g (0.0193 mol/g) of anhydrous diamine ethylene in 35 cm3 of absolute alcohol. The mixture treated as described in Example 3(d) gives 3.5 g (yield: 59.5%) of hydrochloride of (5'-bromo-2'-cyclopropyl)-2$\Delta_2$-phenoxymethyl-imidazoline which, once recrystallized in methanol, melts at 240° C.

EXAMPLE 5

HYDROCHLORIDE OF (5'-METHYL-2'-CYCLOPROPYL)-2-PHENOXYMETHYL-$\Delta_2$-IMIDAZOLINE (I) (R=CH$_3$) (N.D. 83.201)

(a) 5-methyl-2-cyclopropyl-phenoxyacetate of ethyl 6.5 g (0.044 mol/g) of 5-methyl-2-cyclopropyl phenol, 35 cm3 of anhydrous methylethyl ketone, 6.03 g (0.044 mol/g) of dry potassium and 7.66 g (0.063 mol/g) of ethyl chloracetate are introduced in a 100 cm3 three-nozzled flask equipped with a condenser topped with a drying tube filled with calcium chloride, with a sinking thermometer (extending inside the flask) and stirring means. The mixture is heated under stirring for 28 hours at reflux temperature, then it is cooled and the mineral salts are filtered of and washed with 60 cm3 of methyl ethyl ketone; the solvent is evaporated from the filtrate and the residue is dissolved in 50 cm3 of ether, the resulting solution is washed successively twice in 25 cm3 of sodium hydroxyde N, the alkaline washing waters are extracted twice successively with 50 cm3 of ether, and the ethereal extracts are collected, washed twice with 50 cm3 of water, dried over anhydrous sodium sulphate, and filtered, after what the solvent is evaporated from the filtrate and the residue is rectified.

7.4 g (yield=73%) of 5-methyl-2-cyclopropyl-phenoxy acetate of ethyl are obtained in the form of a colorless liquid boiling at 112° C. under 0.5 mm of mercury.

(b) 5-methyl-2-cyclopropyl-N-phenoxy)(B-aminoethyl-)acetamide 5.3 g (0.0316 mol/g) of 5-methyl-2-cyclopropyl-phenoxyacetate of ethyl and 7.6 g (0.126 mol/g) of anhydrous diamine ethylene are introduced in a 50 cm3 three-nozzled flask, equipped with a condenser topped with a drying tube filled with calcium chloride and a sinking thermometer. The mixture is heated for 17 hours at 100° C., and cooled, then 20 cm3 of water are added and a small amount of an insoluble substance is filtered off; then the water and excess of diamine ethylene are evaporated in vacuo. The solid residue is dissolved in 30 cm3 of isopropanol and 5 cm3 of an isopropanol hydrochloric solution 5.18N is added; the solution is iced, the hydrochlorate precipitate is drained, washed with 20 cm3 of isopropanol, dried, and finally recrystallized in 80 cm3 of isopropanol.

3.5 g (yield: 40%) of hydrochlorate of 5-methyl-2-cyclopropyl-N-phenoxy($\beta$-aminoethyl)acetamide, are obtained in the form of a white crysallized compound which melts at between 165° C. and 167° C.

(c) Hydrochloride of (5'-methyl-2'-cyclopropyl)-2-phenoxymethyl-$\Delta_2$-imidazoline To 1.4 g of hydrochlorate of (5-methyl-2-cyclopropyl)-N-($\beta$-aminoethyl)acetamide, are added 50 cm3 of water, 50 cm3 of ether and a saturated solution of sodium carbonate until a pH of 9 is reached. The aqueous phase is decanted, the solvent is evaporated from the ethereal phase and the 0.9 g of solid base mixed with 0.2 g of quicklime are heated for one hour at 200° C. The mixture is left to cool, 5 cm3 of isorpopylic alcohol are added, the insoluble substance is filtered and the filtrate is acidified with a few drops of an isopropanol hydrochloric solution. The imidazoline hydrochlorate which has formed is drained and identified by its melting point and its IR spectrum, with the compound prepared according to Example 1.

The compounds according to the invention have interesting pharmacological properties, such as vasoconstrictor properties which can be advantageously used for the symptomatic treatment of rhinologic disorders with nasal congestion.

(1) The vaso-constrictor properties and potency of the compounds (I) object of the present invention have been investigated and quantified in the anaesthetized pithed rat by determination of their dose-vasodepressor response curves after intravenous administration, according to the technique described by Shipley and Tilden (Proceedings of Society of Experimental Biology, 1947, 64, pages 453–455). This technique allows assessment of the postsynaptic $\alpha$-adrenoceptor agonist properties of a drug. The vaso-constrictor properties of the compounds according to the invention have been compared to those of Cirazoline, the most powerful and specific postsynaptic $\alpha$1-adrenoceptor agonist known up to now, and to those of Fenoxazoline, which is also a postsynaptic $\alpha_1$-adrenoceptor agonist currently sold on the market. For each of these drugs, log of cumulative doses-hypertensive response curves after intravenous administration have been drawn in groups of eight Wistar rats, anaesthetized, pithed, bilaterally vagotomized, atropinized and treated with d-tribocurarine. ED$_{50}$s (doses in mg/kg of the base inducing 50% of the maximal response) were then calculated for each drug and compared to those of the reference compounds.

Table I reports the values of these ED$_{50}$s. It appears from this table that compounds ND 83201 and ND 83204 are the most powerful vaso-constrictor agents, their potency being about 1.75 times that of Cirazoline and three times that of Fenoxazoline.

TABLE I

| Substances | R | ED$_{50}$ ($\mu$g/kg, I.V.) | Relative power towards Cirazoline |
|---|---|---|---|
| CIRAZOLINE | H | 1.105 ± 0.132 | 1 |
| FENOXAZOLINE |  | 1.790 ± 0.147 | 0.62 |
| ND 83 201 (I) | CH$_3$ | 0.630 ± 0.060 | 1.75 |
| ND 83 202 (I) | Br | 4.422 ± 0.329 | 0.25 |
| ND 83 203 (I) | C$_5$H$_{11}$n | 74.182 ± 6.667 | 0.015 |
| ND 83 204 (I) | Cl | 0.644 ± 0.050 | 1.72 |

(2) Nature of the postsynaptic $\alpha_1$-adrenoceptor agonist vasoconstrictor effect of ND 83201

The aforementioned experiments were repeated with ND 83201, Cirazoline and Fenoxazoline, following the same experimental protocol, after prior administration of either a specific postsynaptic $\alpha_1$-adrenoceptor antagonist (prazosine, 20 $\mu$g/kg/min./5 min.), or a specific postsynaptic $\alpha_2$-adrenoceptor antagonist (yohimbine, 60 $\mu$g/kg/min./5 mins.).

For each of the three drugs log of cumulative doses-hypertensive response curves after intravenous administration have been drawn and their ED$_{50}$s (in $\mu$g per kg)

were calculated before and after administration of the antagonists in groups of 8 animals each.

Table II shows the results obtained. These results clearly indicate that the vasoconstrictor effect of ND 83201:

is strongly antagonized by prazosine and even slightly more than those of Cirazoline and Fenoxazoline, is almost not antagonized by yohimbine, as is also the case for Cirazoline and Fenoxazoline.

These results thus clearly demonstrate that ND 83201 is a specific postsynaptic $\alpha_1$-adrenoceptor agonist.

TABLE II

| Substances | $ED_{50}$ (ug/kg, I.V) | $ED_{50}$ (ug/kg,I.V.) after prazosine | $ED_{50}$ after $ED_{50}$ before prazosine | $ED_{50}$ (ug/kg,I.V.) after yohimbine | $ED_{50}$ after $ED_{50}$ before yohimbine |
|---|---|---|---|---|---|
| Cirazoline | 1.105 ± 0.132 | 8.568 ± 0.721 | 7.75 | 1.180 ± 0.108 | 1.05 |
| Fenoxazoline | 1.790 ± 0.147 | 16.205 ± 1.240 | 9.05 | 1.804 ± 0.237 | 1.01 |
| ND 83 201 | 0.630 ± 0.060 | 7.284 ± 0.974 | 11.56 | 0.805 ± 0.076 | 1.25 |

(3) Other pharmacological properties

TABLE III

| | HEARTBEAT FREQUENCY | | | |
|---|---|---|---|---|
| Tested substance (μg/kg, I.V.) | Before medullar electric stimulation | Under electric stimulation (supramaximal tachycardia | Under electric stimulation and after clonidine 40 μg/kg, I.V. | Under electric stimulation after clonidine and tested substance |
| Phentolamine (700)* | 355.0 ± 10.1 | 455.6 ± 11.5 | 411.2 ± 8.9 | 452.5 ± 10.6 |
| Prazosine(700)* | 338.7 ± 6.3 | 440.0 ± 9.6 | 391.9 ± 8.2 | 388.1 ± 7.0 |
| Cirazoline(2.5)* | 360.7 ± 13.1 | 452.1 ± 10.5 | 395.7 ± 14.1 | 403.6 ± 14.8 |
| ND 83 201 (18.5)* | 350. ± 4.0 | 448.7 ± 7.7 | 391.2 ± 5.9 | 403.1 ± 6.0 |

*The indicated doses are those which have caused the maximal effect.

(a) ND 83201 is a directly acting $\alpha_1$-adrenoceptor agonist. Thus, its vasoconstrictor effects, like those of cirazoline and fenoxazoline, are not, except in very high doses, modified by a pre-treatment of the animals with reserpine, the experimental protocol being the same as that used in the preceeding experiments.

(b) ND 83 201 has no presynaptic $\alpha_2$-adrenoceptor agonist activity.

The technique used is that of the anaesthetized, pithed bivagotomized, atropinized and curarized Wistar rat, the spinal cord of which is electrically stimulated (Gillespie and Muir—British Journal of Pharmacology and Chemotherapy, 1967, 30, pages 78-87) in its thoracic portion in order to induce submaximal tachycardia. In this type of experiments, the presynaptic $\alpha_2$-adrenoceptor agonists, such as clonidine, reduce the induced tachycardia.

ND 83201 and Cirazoline have therefore been investigated in this experimental model, comparatively to clonidine, in groups of 8 animals each. Whereas clonidine reduced the submaximal tachycardia (effect antagonized by yohimbine), neither ND 83201, nor Cirazoline, exhibited the slightest effect, thus demonstrating that they were completey devoid of any presynaptic $\alpha_2$-adrenoceptor agonist activity.

(c) ND 83201 has no presynaptic $\alpha_2$-adrenoceptor antagonist activity.

The technique used is that of the anaesthetized, pithed, bivagotomized, atropinized and curarized Wistar rat, the spinal cord of which is stimulated (Gillespie and Muir—British Journal of Pharmacology and Chemotherapy, 1967, 30, p. 78-87)) as described hereinabove to induce a submaximal tachycardia. This tachycardia is then reduced by administration of a presynaptic $\alpha_2$-adrenoceptor agonist, clonidine (40 ug/kg, I.V.).

In this type of experiments presynaptic $\alpha_2$-adrenoceptor antagonists such as phentolamine, but not $\alpha_1$-adrenoceptor antagonists such as prazosine, restore the submaximal tachycardia.

ND 83201 and Cirazoline were investigated in this experimental protocol and compared to phentolamine and prazosine in groups of 8 animals each.

Table III shows the results obtained. Whereas phentolamine resores sub-maximal tachycardia, prazosine, ND 83201 and Cirazoline had no effect. This demonstrates that ND 83201 and Cirazoline have no presynaptic $\alpha_2$-adrenoceptor antagonist properties, just like prazosine.

(d) ND 83201 has no $\beta$-adrenoceptor postsynaptic agonist activity. Indeed, in the same experimental protocol as that used in the preceeding experiments, the $ED_{50}$ of ND 83201 is not modified by a pretreatment with a $\beta$-adrenoceptor antagonist (propranold, 150 μg/kg/min/5 min.).

In conclusion, ND 83201 and ND 83 204 are powerful peripheral vasoconstrictor agents, about 1.75 times more potent than Cirazoline.

Regarding ND 83201, these vasoconstrictor properties result from the specific and direct postsynaptic $\alpha_1$-adrenoceptor agonist effects of the drug, as is also the case for Cirazoline.

Moreover, ND 83201, just like Cirazoline, has no postsynaptic $\alpha_2$-adrenoceptor agonist, presynaptic $\alpha_2$-adrenoceptor agonist and presynaptic $\alpha_2$-adrenoceptor antagonist properties.

The above results show that the compounds (I) according to the invention exhibit more potent and more specific vasoconstrictor effects at the level of postsynaptic $\alpha_1$-adrenoceptors than any of the currently known drugs.

These particularly interesting properties make it possible to use the compounds (I) according to the invention as nasal vasoconstrictor and congestion-reliever drugs, especially for the treatment of various rhinological syndromes, in human and veterinary therapy.

Given their postulated therapeutic indications and their predictable dosage, the compounds according to the invention can be considered as devoid of any toxicity.

The products to the invention can be presented in any of the normal pharmaceutical forms, and in particular in solution for nasal drops, or sprays, optionally associated to other active principles.

The presentation as a spraying solution is particularly adapted to this type of medecine and the good stability of the aqueous solutions of the products according to the invention is a considerable advantage over other medecines of the same type.

A study of stability made comparatively to Cirazoline, keeping simultaneously aqueous solution at 1°/oo of this compound and of ND 83204 at the same concentration, at room temperature, has revealed after a few days the appearance of the cleaving product by hydrolysis of the imidazoline cycle, namely the amino-amide (V) in the case of Cirazoline, whereas in the case of the ND 83 204, even after one month, no trace of hydrolysis is yet detectable.

We claim:

1. Imidazoline of the formula (I)

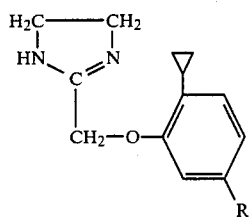

in which R is one of the group consisting of methyl or chlorine, or the addition salt of said imidazoline with a pharamaceutically acceptable acid.

2. Imidazoline salt according to claim 1, wherein said salt is obtained with an acid selected from:
prednisolone-21-benzoyl-metasulphonic acid, 9α-fluoro-16β-methyl-11β,17α,21-trihydroxy-1,4-pregnadiene-3,20-dione-21-orthophosphoric acid, 11β,17α,21-trihydroxy-1,4-pregnadiene-3,20-dione-21-orthophosphoric acid, and 11β,17α,21-trihydroxy-4-pregnene-3,20-dione-21-succinic acid.

3. A composition useful to treat a patient with a rhinological syndrome associated with a disease responsive to a postsynaptic alpha-adrenoreceptor agonist or a patient who is in need of a nasal vasoconstrictor or a congestion reliever, said composition comprising a carrier and an effective amount of an imidazoline of the formula:

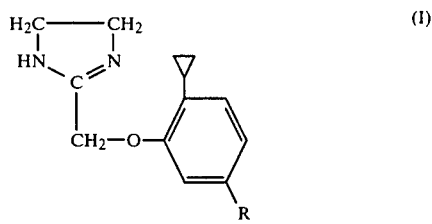

in which R is one of the group consisting of chlorine or methyl or the acid addition salt of said imidazoline with a pharmaceutically acceptable acid.

4. A method for treating a patient with a rhinological syndrome associated with a disease responsive to a postsynaptic alpha-adrenoreceptor agonist or a patient who is in need of a nasal vasoconstrictor or a congestion reliver, said method comprising administering to said patient an effective amount of a composition comprising a carrier and an effective postsynaptic alpha-adrenoreceptor agonizing amount of an imidazoline of the formula:

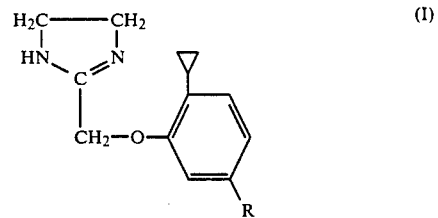

in which R is one of the group consisting of chlorine or methyl or the acid addition salt of said imidazoline with a pharmaceutically acceptable acid.

* * * * *

UNITED STATES PATENT AND TRADEMARK OFFICE
CERTIFICATE OF CORRECTION

PATENT NO. : 4,663,340

DATED : May 5, 1987

INVENTOR(S) : NAJER, Henry et al

It is certified that error appears in the above-identified patent and that said Letters Patent is hereby corrected as shown below:

Column 12, line 24, delete "reliver" and replace therefor --reliever--.

Signed and Sealed this

Fifteenth Day of September, 1987

Attest:

DONALD J. QUIGG

Attesting Officer

Commissioner of Patents and Trademarks